United States Patent [19]

Richter, Jr. et al.

[11] Patent Number: 4,514,627
[45] Date of Patent: Apr. 30, 1985

[54] PETROLEUM STREAM ANALYZER

[75] Inventors: Albert P. Richter, Jr., Houston; Ronald L. Campsey, Alief; Hans J. Paap, Houston; Alfred E. Bussian, Spring, all of Tex.

[73] Assignee: Texaco Inc., White Plains, N.Y.

[21] Appl. No.: 579,315

[22] Filed: Feb. 13, 1984

Related U.S. Application Data

[63] Continuation-in-part of Ser. No. 351,699, Feb. 24, 1982.

[51] Int. Cl.$^3$ ............................................. G01V 5/00
[52] U.S. Cl. ................................. 250/255; 250/359.1
[58] Field of Search ............ 250/255, 269, 270, 358.1, 250/359.1, 360.1

[56] References Cited

U.S. PATENT DOCUMENTS

| | | | |
|---|---|---|---|
| 4,171,485 | 10/1979 | Marshall | 250/359.1 |
| 4,200,789 | 4/1980 | Arnold et al. | 250/270 |
| 4,209,695 | 6/1980 | Arnold et al. | 250/270 |
| 4,354,110 | 10/1982 | Richter, Jr. et al. | 250/359.1 |
| 4,365,154 | 12/1982 | Arnold et al. | 250/270 |

*Primary Examiner*—Alfred E. Smith
*Attorney, Agent, or Firm*—Robert A. Kulason; James J. O'Loughlin; Ronald G. Gillespie

[57] ABSTRACT

A petroleum stream analyzer includes a test cell having a petroleum stream, or portion thereof, flowing through it. A neutron source bombards the petroleum stream in the test cell with fast neutrons, which are slowed down and thereafter engaged in thermal neutron capture reaction with materials in the petroleum stream. Gamma ray apparatus including a gamma ray detector provides an energy spectra of gamma rays from the materials in response to the capture of the thermal neutrons by the materials in the petroleum stream. Shielding material separates the neutron source from the gamma ray detector and a housing located within the test cell houses the neutron source, the gamma ray detector and the shielding material in a manner so that a longitudinal axis of the housing, which is substantially aligned with the axial flow of the petroleum stream in the test cell, passes through the neutron source, the shielding material and the gamma ray detector. The anaylzer also includes apparatus which derive a measure of a characteristic of the petroleum stream in accordance with the obtained gamma ray energy spectra of the materials in the petroleum stream.

6 Claims, 2 Drawing Figures

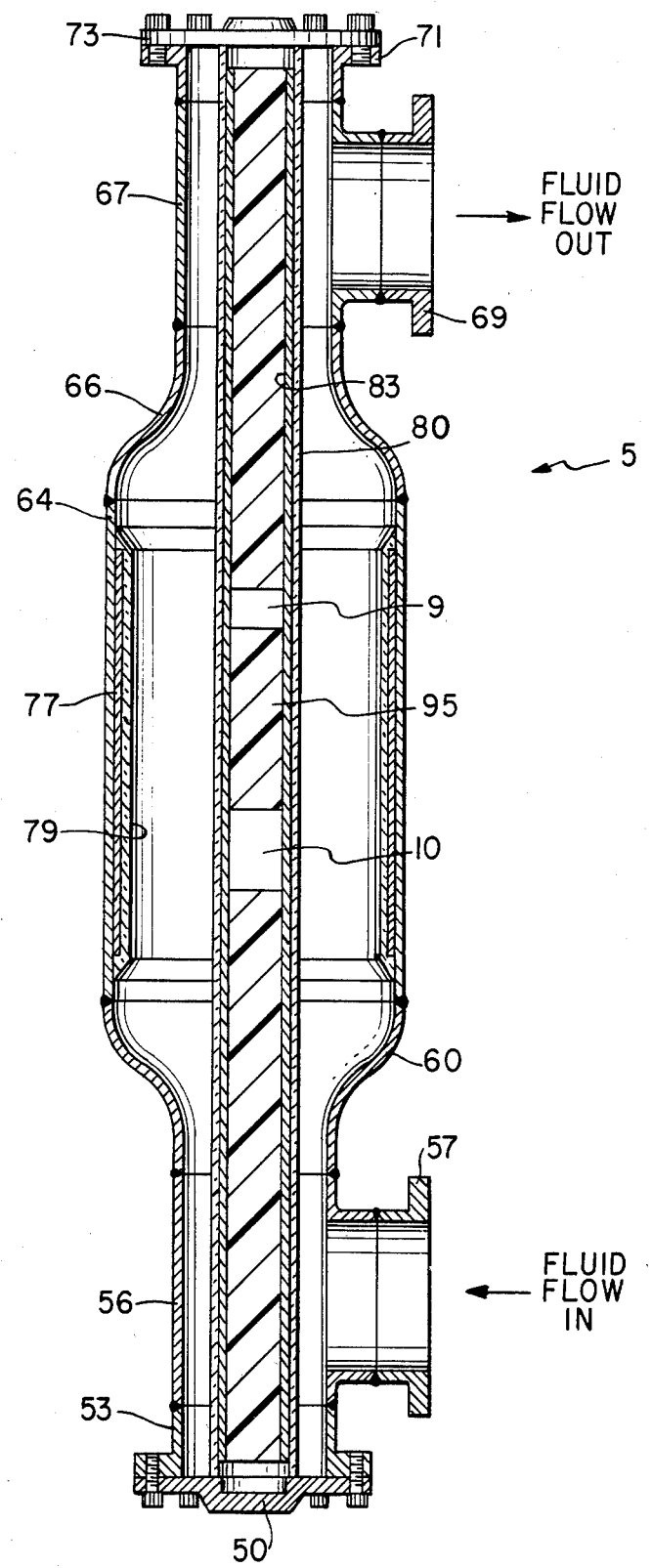

PETROLEUM STREAM ANALYZER

CROSS-REFERENCE TO RELATED APPLICATIONS

This application is a continuation as to all subject matter common to U.S. application Ser. No. 351,699, filed on Feb. 24, 1982, by Albert P. Richter, Jr., Ronald L. Campsey, Hans J. Paap and Alfred E. Bussian and assigned to Texaco Inc., assignee of the present invention; and a continuation-in-part for all additional subject matter.

BACKGROUND OF THE INVENTION

Field of the Invention

The present invention relates to an analyzer in general and, more particularly, to a petroleum stream analyzer utilizing radiation techniques.

SUMMARY OF THE INVENTION

A petroleum stream analyzer includes a test cell having a petroleum stream, or portion thereof, flowing through it. A neutron source bombards the petroleum stream in the test cell with fast neutrons which are slowed down and thereafter engaged in thermal neutron capture reaction with materials in the petroleum stream. A gamma ray device provides a gamma ray energy spectrum of the material in response to the capture of the thermal neutrons by the material in the petroleum stream. The gamma ray device is shielded by shielding material. A housing houses the neutron source and shielding material and the gamma ray device and is located in the test cell in a manner so that a longitudinal axis of the housing passes through the neutron source, the shielding material, and the gamma ray device and is substantially aligned with the axial flow of the petroleum stream in the test cell. Apparatus derives a measure of a characteristic of the petroleum stream in accordance with the obtained gamma ray energy spectra of the materials in the petroleum stream.

The objects and advantages of the invention will appear more fully hereinafter from a continuation of the detailed description which follows, taken together with the accompanying drawings wherein true embodiments of the invention are illustrated by way of example. It is to be expressly understood, however, that the drawings are for illustration purposes only and are not to be construed as defining the limits of the invention.

DESCRIPTION OF THE DRAWINGS

FIG. 2 is a detailed drawing of the test chamber shown in FIG. 1.

DESCRIPTION OF THE INVENTION

Figure 1:
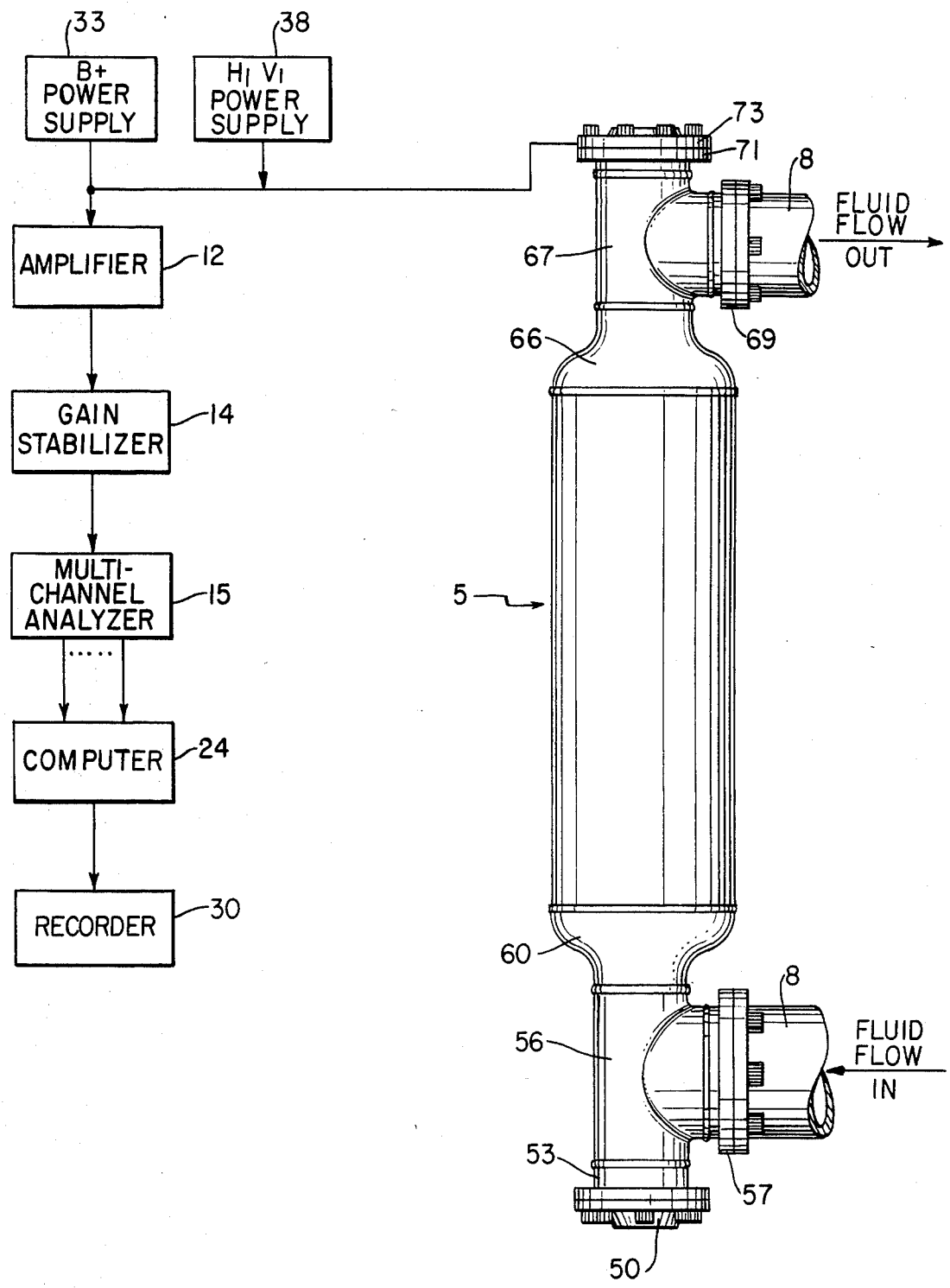
FIG. 1 is a simplified block diagram of a petroleum stream analyzer constructed in accordance with the present invention.

Relatively small concentrations of salt in crude oil can often cause major problems in the crude oil refining process. The present invention relates to the detection in a flowing crude oil stream or other petroleum conduit of concentrations of salt. The present invention is based upon the bombardment or irradiation of a flowing stream of crude oil with neutrons and the detection of gamma radiation admitted by the element chlorine upon capture of thermal neutrons. For a given thermal neutron flux, the yield of chlorine capture radiation is proportional to the concentration of chlorine in the flowing stream of crude oil. If it is known or assumed that all chlorine is in the form of NaCl, or other chloride form, then the intensity of chlorine captured radiation is a direct indication of salt concentration.

Gamma radiation resulting from thermal capture reactions is "prompt" in the sense that it is admitted within microseconds after the capture event. This is in contrast to "delayed" gamma radiation resulting from "activation" type reactions which is admitted from milliseconds to years after the reaction. Since thermal neutron capture radiation is almost instantaneous, the velocity and volume flow rate of the crude oil stream do not effect the measurement.

A salt-in-crude monitor such as disclosed and described in U.S. Pat. Nos. 4,209,695 and 4,200,789 involve the use of the foregoing radiation techniques in determining the salt content in a production stream of crude oil. The present invention is a improvement of the inventions of those patents by utilizing an in-line test tapping chamber.

Referring now to FIG. 1 a production stream of crude oil flows through a pipe line 8 which is connected to a test chamber 5 and out again through another pipe line 8. Test chamber 5 has within it a neutron source 9 and a gamma ray detector assembly 10. Neutron source 9 irradiates the production stream with neutrons. Gamma ray detector assembly 10 provides pulses corresponding in height and frequency to the detected gamma radiation. Detector assembly 10 periodically provides reference pulses. The pulses from detector assembly 10 are provided to an amplifier 12. It should be noted that the wires connecting detector assembly 10 to amplifier 12 are not shown in FIG. 2 so that the details of construction of test chamber 5 can best be shown. The output is amplified and provided to a gain stabilizer 14 which in turn provides the stablized signal to a multi-channel analyzer 18. Multi-channel analyzer 18 provides a plurality of signals corresponding to the test counts of various levels of energy. The signals from the multi-channel analyzer 18 are provided to a computer 24 which provides its output to a recorder 30. The details of operation of amplifier 12, gain stabilizer 14, multi-channel analyzer 18, computer 24 and recorder 30 are fully described in the foregoing patents and are not necessary to an understanding of the present invention. A B+ power supply 33 and a high voltage power supply 38 provide the necessary operating voltages to neutron source 9 and gamma ray detector assembly 10.

With reference to FIG. 2, test chamber 5 includes an end cap 50 affixed to an adaptor 53 which is welded to a T fitting 56. Another adaptor 57 is also welded to T fitting 56 and the remaining opening of T fitting 56 is welded to a bell reducer 60. A length of iron pipe 64, adapted as hereinafter explained, is welded to bell reducer 60 and to another bell reducer 66. Bell reducer 66 is in turn welded to a T fitting 67 having an adaptor 69 welded to it for connection to pipe line 8. Another adapter 71 is also welded to T fitting 67 for connection to an end plate 73.

Pipe 64 has mounted on its internal side, boron carbide (B4C) layer 77 which in turn has an epoxy glass lining 79 coated thereon on it. Due to boron's large thermal neutron capture crosssection, the boron carbide layer effectively shields iron pipe 64 from neutrons thermalized (slowed down) within the petroleum stream. Thermal neutron capture gamma ray energies from boron are less than about 0.514ev whereas those from iron extend into the high energy region where the thermal capture gamma rays from chlorine and sulfur are measured. Therefore, without the shielding action of the boron carbide layer the gamma rays from the iron pipe would contribute a substantial "background noise" to the energy levels at which the monitor of the aforementioned U.S. patent monitors the chlorine and sulfur gamma rays. This "background noise" would interfere with the accurate determination of chlorine and sulfur within the petroleum stream and essentially would prevent their determination of low levels of chlorine and sulfur altogether.

End plate 73 has affixed to it an epoxy glass sleeve 80 with an internal boron carbide sleeve 83. If more rigidity is desired, a steel sleeve may be inserted inside of boron carbide sleeve 83. Mounted within the passageway is a neutron source 9, shielding material 95 and a gamma ray detector assembly 10. Shielding material 95 is made form machineable hard plastic coated with boron carbide on its surfaces. Neutron source 9 and detector assembly 10 are maintained in a predetermined position within boron carbide sleeve 83 by shielding material 101 and 102. Again shielding material 101 and 102 are made from machineable hard plastic coated with boron carbide on its surfaces. The electrical connections for neutron source 9 and the gamma ray detector assembly 10 are not shown for convenience. In operation, with the petroleum stream flowing through it, neutron source 9 is activated and bombards the petroleum stream which yields gamma radiation as hereinbefore explained. Gamma ray detector assembly 10 detects the gamma radiation and provides an output signal in accordance with detected gamma rays for the analysis of the salt content of the production stream as set forth in the aforementioned U.S. patent.

The test chambers disclosed in the foregoing U.S. patents use the fluid to be measured as a shield between detector and source. As the hydrogen index of the fluid decreases, e.g. increasing gas content, the fluid loses its neutron moderating and gamma ray shielding characteristics. This loss of shielding allows neutrons with source energies and/or near source energies and gamma rays from the source to reach the detector and contribute to undesirable background effects. The present invention uses shielding material to prevent direct transmission of above neutrons and gamma rays to the detector.

The present invention allows easy change of spacing between neutron source 9 and gamma ray detector assembly 10 to optimize measurement of fluids with various neutron moderating (hydrogen index) characteristics. The spacing is controlled or changed by changing the length of shielding material 95 between source 9 and assembly 10 whereas in the aforementioned U.S. patents, the distance is fixed. Further, at the very least, a change in the size of the test chamber would be required to change the spacing. The aforementioned U.S. patents use the petroleum stream itself as the shielding material. The present invention improves upon this by using special shielding material which can be exchanged to optimize the response for various crudes and parameters to be measured.

It should also be noted that the present invention allows the simultaneous use of more than one detector spaced at different distances from the source. The responses of the detectors can then be combined to obtain fluid characteristics such as hydrogen index or gas content by ratio methods.

What is claimed is:

1. A petroleum stream analyzer comprising
   a test chamber having a petroleum stream, or a portion thereof, flowing through it,
   means for bombarding the petroleum stream in the test chamber with fast neutrons, which are slowed down and thereafter engaged in thermal-neutron capture reactions with materials in the petroleum stream,
   means for obtaining gamma-ray energy spectra of the materials in response to the capture of the thermal-neutrons by the materials in the petroleum stream,
   shielding means for shielding said obtaining means from neutrons provided by said bombarding means,
   housing means for housing the bombarding means, the shielding means and the obtaining means, said housing means being located in said test chamber in a manner so that a longitudinal axis of said housing means passes through said obtaining means, shielding means and bombarding means, and is substantially aligned with the axial flow of the petroleum stream in said test chamber, and
   means for deriving a measure of a characteristic of the petroleum stream in accordance with the obtained gamma-ray energy spectra of the materials in the petroleum stream; and
   said test chamber includes
   a shell,
   at least two adaptor means affixed to the shell for passing the petroleum stream, or a portion thereof, into and out of the shell, and
   at least two end plates affixed to opposite ends of said shell, with one end plate having the housing means attached thereto.

2. An analyzer as described in claim 1 in which the housing means is affixed to the one end plate so that the housing is readily removable from said end plate and the one end plate is affixed to said shell so that the end and housing are readily removable from said shell.

3. An analyzer as described in claim 2 in which the shell has one inner lining of boron carbide and another inner lining of epoxy glass arranged with the boron carbide lining so that the boron carbide lining is between the epoxy glass lining and said shell.

4. An analyzer described in claim 3 in which the housing is made of epoxy glass and has an inner lining of boron carbide and has a length sufficient to reach from the one end plate, that the housing is affixed to, butt up against the other end plate so that the housing is held rigidly in place within said shell.

5. An analyzer as described in claim 4 in which the obtaining means includes
   detector means for detecting gamma radiation and providing electrical pulses in accordance with the detected gamma radiation and for providing reference pulses,
   amplifier means located outside said test chamber and electrically connected to said detector means for amplifying said electrical pulses from said detector means,
   gain stabilizing means connected to said amplifier means for stabilizing the amplitude of said amplifying pulses in accordance with the reference pulses,
   multichannel analyzing means connected to said gain stabilizer means for providing a plurality of outputs in accordance with the energy levels of the amplified pulses and, computer means connected to the multichannel analyzing means for providing an output representative of the gamma ray spectra of the materials in the petroleum stream flowing through the test chamber in accordance with the outputs from the multichannel analyzer.

6. An analyzer as described in claim 5 in which the indicating means is a recorder connected to the computer means which provides a record of the gamma ray spectra in accordance with the output from the computer means.

* * * * *